United States Patent [19]

de Juan, Jr. et al.

[11] Patent Number: 5,047,008

[45] Date of Patent: Sep. 10, 1991

[54] VITRECTOMY PROBE

[75] Inventors: Eugene de Juan, Jr., Durham, N.C.; Gerald S. Gahn; John J. Weidenbenner, both of Manchester, Mo.; Dyson Hickingbotham, Bahama, N.C.

[73] Assignee: Storz Instrument Company, St. Louis, Mo.

[21] Appl. No.: 428,125

[22] Filed: Oct. 27, 1989

[51] Int. Cl.$^5$ ............................................. A61B 17/20
[52] U.S. Cl. ..................................... 604/22; 128/751; 606/171
[58] Field of Search ................... 604/22; 128/751–754; 606/170, 171

[56] References Cited

U.S. PATENT DOCUMENTS

| | | | |
|---|---|---|---|
| 3,815,604 | 6/1974 | O'Malley et al. | 604/22 |
| 4,210,146 | 7/1980 | Banko | 606/171 |
| 4,577,629 | 3/1986 | Martinez | 604/22 |
| 4,696,298 | 9/1987 | Higgins et al. | 604/22 |
| 4,753,234 | 6/1988 | Martinez | 604/22 |
| 4,909,249 | 3/1990 | Akkas et al. | 604/22 |
| 4,940,468 | 7/1990 | Petillo | 604/22 |

Primary Examiner—Stephen C. Pellegrino
Assistant Examiner—Michael Rafa
Attorney, Agent, or Firm—Brooks & Kushman

[57] ABSTRACT

An improved vitrectomy probe for removing vitreous and other fibrous gel materials. A hollow cutting blade is reciprocated within a smooth bore hollow needle of the microsurgical vitrectomy probe across a cutting edge of the outer needle slicing the fibrous material of the vitreous. A pressurized fluid source, diaphragm and spring cooperate to provide for the reciprocation of the blade. A vacuum source removes vitreous material through the hollow needle. A reciprocating suction outlet tube attached to the hollow needle directs vitreous material into a vacuum fitting which is isolated from the motion of the reciprocating outlet tube. An adjustment screw limits the travel of the reciprocating blade as well as the size of the opening in the needle. A dissector head faciitates the separation of vitreous fibers and directs them into the needle opening.

26 Claims, 2 Drawing Sheets

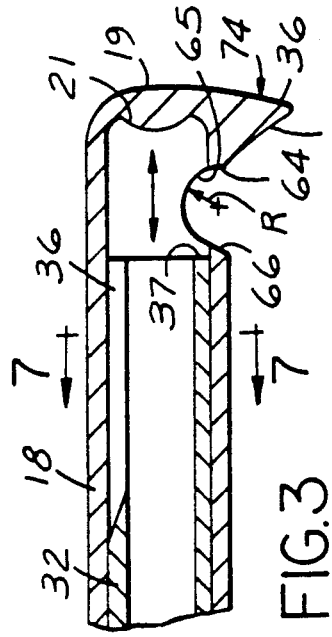
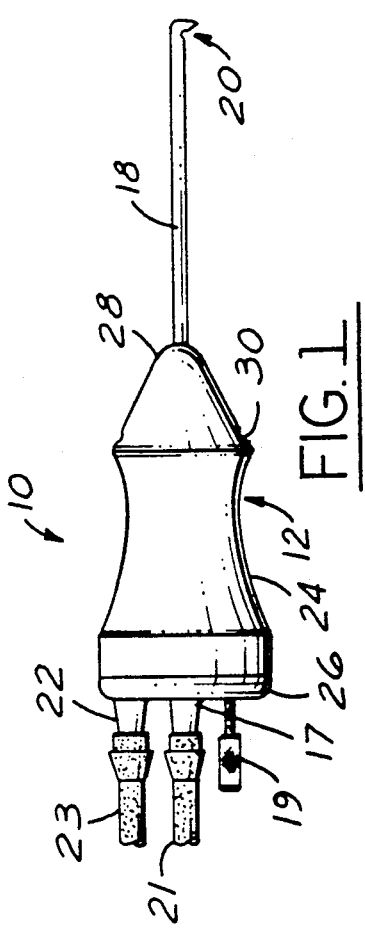
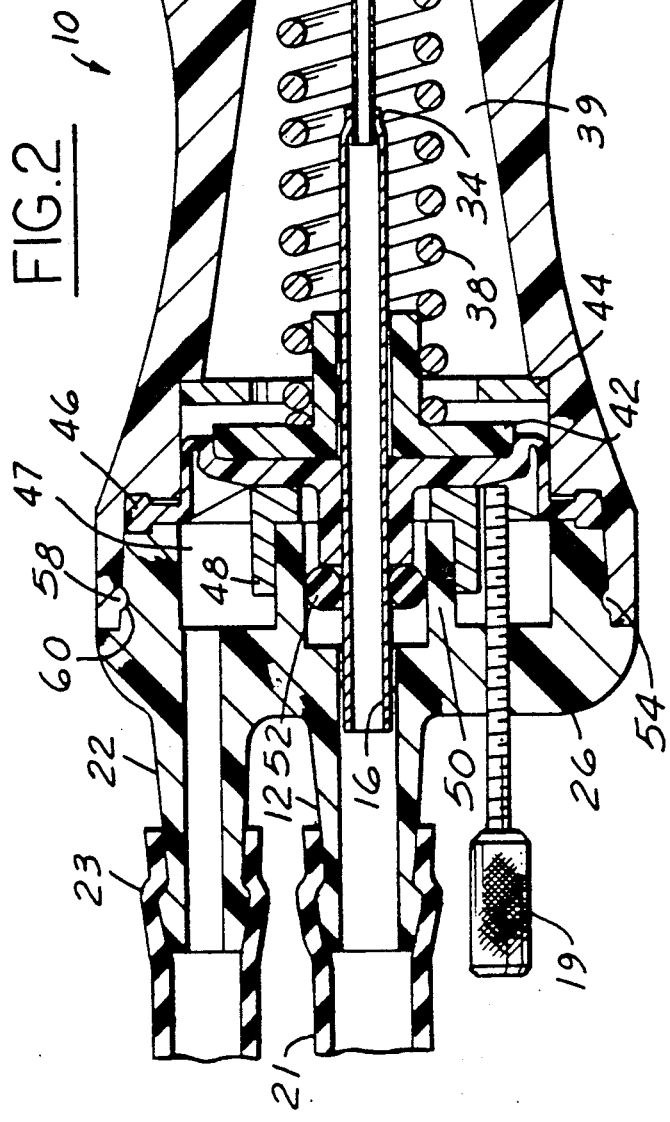

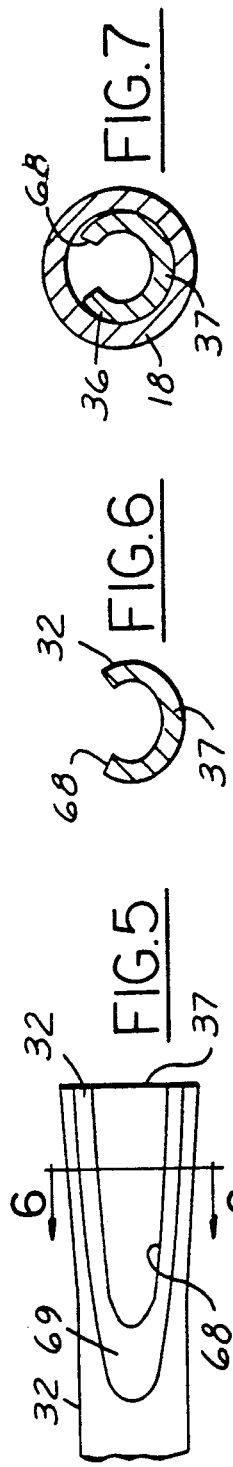
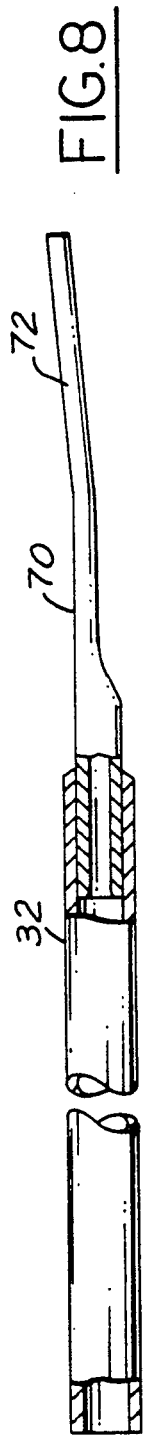
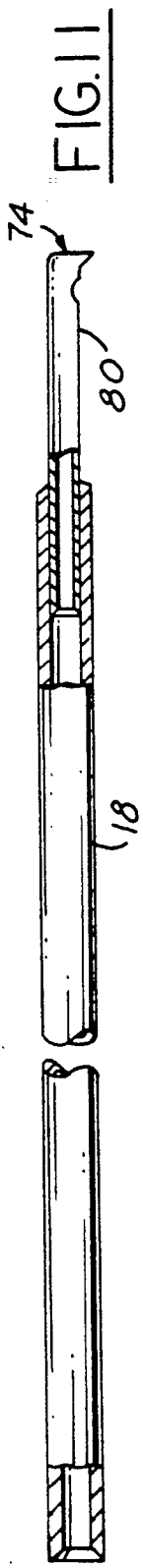

VITRECTOMY PROBE

BACKGROUND OF THE INVENTION

Cross-Reference to Related Applications

The present invention is related to the subject matter of the following commonly assigned application being filed concurrently on even date herewith:

Application Ser. No. 428,232 filed Oct. 27, 1989 entitled "Control System for Ophthalmic Surgical Instruments."

The disclosure of the above-referenced application is hereby incorporated by reference.

Field of the Invention

The present invention relates to improved surgical instruments for use in ophthalmic surgery, particularly to microsurgical cutting probes used to remove the vitreous from an eye. One useful prior art vitrectomy probe is disclosed in U.S. Pat. No. 4,696,298.

Description of Related Art

There are ophthalmic surgical procedures which require the removal of all or a part of the vitreous humor in the eye. The vitreous humor (or "vitreous") is a colorless transparent jelly-like material that fills the area of the eye posterior to the crystalline lens. The vitreous is filled with numerous fiber-like materials which are often attached to the retina. Removal of the vitreous is difficult due to the presence of the fibers and the possibility of detachment of the inflexible and very delicate retina.

The present invention provides an improved microsurgical cutting instrument with an elongated needle or probe which is adapted to cut the fibers within the vitreous and remove the vitreous from the eye. The vitreous is removed primarily through the use of a suction through the hollow probe needle which is inserted through an incision in the eye, under the direction of a surgeon using a microscope.

During ophthalmic microsurgery, several surgical probes and instruments may be used, such as cutting tools and irrigation/aspiration instruments. The surgical systems also contain a switch or switches (usually foot activated switches operated by the surgeon) controlling the suction and liquid flow and a remote base unit which houses the suction and pumping mechanisms, and containers for storing irrigation liquid and collected material. The ophthalmic surgeon controls the positioning and functioning of the instruments in the eye through the use of a microscope.

The basic concept and operation of a vitrectomy probe combines a constant suction with a repeated cutting motion of a blade. The probe comprises a stationary outer needle which contains one or more apertures to receive the vitreous when suction is applied. A cutting blade located within the outer needle cuts the fibers of the vitreous as it is drawn into the needle. Various types of cutting mechanisms are known today including rotating or reciprocating blades.

In some vitrectomy probes utilizing reciprocating blades, a reciprocating blade within the needle is attached directly to a tube from a vacuum means. This sometimes creates undesirable motion in the vacuum line which may interfere with steady hand positioning of the probe by the ophthalmic surgeon. Further, while it is desirable to cut and remove fibrous material immediately adjacent the delicate retina, the force of suction through the needle opening is sometimes not sufficient to direct such fibers into the opening. As a result, it is sometimes difficult to remove fibers close to the retina without excessively disturbing the retina. This problem is particularly acute in vitrectomy probes where the opening is in the side of the needle, a slight distance away from the needle end. This distance may make it difficult to draw vitreous immediately adjacent the retina into the probe.

In addition, while the force of suction and the speed of the cutting is typically adjustable in vitrectomy probes, more precise control over the aspiration and cutting would be desirable to account for varying fiber texture size and desired aspiration rate. For example, in some areas it may be desirable to aspirate the vitreous at relatively high volume, such as in the central portion where there are no adjacent structures. In other situations, for example, near the retina, it may be desired to perform the cutting and aspiration of finer textured fibers at lower volumes. Merely controlling the speed of reciprocation of the blade and the suction force may not be entirely satisfactory to give the desired degree of control of cutting and aspiration of the vitreous in all circumstances.

SUMMARY OF THE INVENTION

The present invention comprises a microsurgical probe instrument which comprises an outer needle containing an aperture and an inner hollow tubular member having a cutting blade on one end which is reciprocated within the outer needle. The tubular member, containing the blade, reciprocates inside the outer tube across the aperture in a shearing or scissors like action, slicing the fibrous portion of the vitreous as it is drawn into the aperture of the outer tube. The cutting action is obtained when the squared sharp edge of the blade passes over the sharp lower edge of the aperture in the outer needle.

The present invention involves an improved vitrectomy probe including an outer needle end which contains a transversely protruding pointed extractor or dissector which permits vitreous fibers to be separated from other fibers and from adjacent structures, to thereby facilitate their entry into the aperture. Also, more precise control over aspiration is achieved by means of a reciprocating blade motion adjustment that limits the travel of the tubular member containing the blade on its return stroke to a predetermined point to control the size of the aperture in the needle. Further, control of the position of the vitrectomy probe by the ophthalmic surgeon is improved by providing a vacuum fitting that is isolated from the reciprocating motion of the tubular member containing the blade.

It is an object of the present invention to provide a more easily controlled microsurgical vitrectomy probe for the removal of the vitreous. It is another object of the present invention to provide an improved needle tip for a vitrectomy probe that facilitates the separation of vitreous fibers.

A further object of the present invention to provide a vitrectomy probe which provides for improved control of the aspiration by permitting adjustment of the needle aperture size.

Other objects, features and advantages of the present invention will become apparent from the subsequent description and the appended claims taken in conjunction with the accompanying drawings.

DESCRIPTION OF THE DRAWINGS

FIG. 1 is a side view of a microsurgical probe in accordance with the present invention;

FIG. 2 is a cross-sectional view of the probe of FIG. 1;

FIG. 3 is an enlarged cross-sectional view of the needle, blade, and dissector of the probe of FIGS. 1 and 2;

FIG. 4 is a plan view of the dissector and suction and cutting aperture in the end of the probe needle;

FIG. 5 is a top view of the blade end of the inner hollow tubular member of FIGS. 2 and 3;

FIG. 6 is a cross-sectional view of the blade of FIG. 5 taken along line 6—6 in FIG. 5;

FIG. 7 is a cross-sectional view of the needle and blade mechanism taken along line 7—7 in FIG. 3;

FIG. 8 is a view, partially in cross-section, of a blade mechanism in accordance with an alternate embodiment of the present invention;

FIG. 9 is a side view of the alternate blade mechanism shown in FIG. 8;

FIG. 10 is an end view of the tip of the alternate blade mechanism shown in FIG. 9;

FIG. 11 is a side view, partially in cross-section of the needle in accordance with an alternate embodiment of the present invention;

FIG. 12 is an end view of the needle shown in FIG. 11; and

FIG. 13 is an enlarged cross-sectional view of detailed portions, of the needle shown in FIG. 12.

DETAILED DESCRIPTION OF THE PREFERRED EMBODIMENTS

Referring to various Figures of the drawing, wherein like reference characters refer to like parts, there is shown generally at 10 in FIG. 1 a vitrectomy probe for use in ophthalmic surgical applications. The probe shown in FIG. 1 is suitable for use with compatible microsurgery systems known in the art and is adapted to be disposable after one complete surgical operation.

The probe 10 generally comprises a housing 12 from which extend a vacuum fitting 17, a fluid inlet fitting 22, a blade travel adjustment screw 19, and a probe needle 18 containing a vitreous inlet aperture or port 20. A fluid inlet tube 23 connects the fluid inlet port 22 to a pressurized fluid supply (not shown). A vacuum tube 21 connects vacuum fitting 17 to a vacuum source (not shown). The housing 12 may be constructed from a polysulfone resin and comprises a fingergrip portion 24, a nose 28 which contains air vents 30, and a cap 26.

As shown in more detail in FIG. 2, the probe 10 supports the outer probe needle 18 in the front (nose) 28 of the housing 12. The probe needle may be a T304 stainless steel needle, 500 polish; this needle has been found to have a sufficiently smooth interior bore. Inserted within the probe needle 18 is a hollow inner tubular member 32 which extends into the fingergrip portion of the housing 12. A cutting blade 36 is located on the outer end of the tubular member 32. The tubular member 32 is attached to the end of a suction outlet tube 16 by any conventional means 34, such as crimping, brazing, or the like. The entire blade, inner tubular member and suction outlet tube assembly is reciprocable such that the blade 36 may be slid across the port 20 in the outer needle 18. The blade 36, tubular member 32 and suction outlet tube 16 are automatically returned by the spring means 38 to an open position whereby the port 20 is open. The spring is preferably a 1/32 diameter stainless steel wire compression spring. The spring 38 is contained within the housing of the probe and is supported by a polysulfone O-ring retainer 40 and acts upon a flanged collar retainer 42 through which has been inserted the inner tubular member 32 and suction outlet tube 16.

The length of the cutting motion is limited by an aluminum stop washer 44 which contacts the retainer 42 at the end of the cutting stroke. The housing 12 is divided by a diaphragm 46 into a spring chamber 39 and a fluid chamber 47. The diaphragm 46 abuts against the diaphragm stop 48 which fits over the inwardly extending flange 50 of the cap 26 when the blade 36 and suction outlet tube 16 are in the open position.

It has been found that more precise control over the aspiration process can be achieved by limiting the travel of the blade 36 to restrict the size of the inlet port 20. In accordance with the present invention, a blade travel adjustment screw 19 is threaded into the cap 26 so that the tip of the adjustment screw 19 makes contact with the diaphragm 46. The adjustment screw 19 may then be rotated by hand to press the diaphragm 46, retainer 42, outlet tube 16, inner tube 32 and blade 36 to a partially closed position. As a result, the size of the opening 20 and the total travel of the blade 36 will be reduced. A reduced size opening 20 and restricted blade travel will increase the velocity and reduce the volume of the aspiration of vitreous. This may be useful for working in delicate areas and where increased suction distance is required.

The fluid chamber 47 is sealed substantially fluid tight by an O-ring 52. Alternatively, a pair of O-rings may be used. The fluid inlet fitting 22 is connected to a controlled supply of a pressurized fluid (not shown) through inlet tube 23. The cap 26 contains a groove 54 along its outer rim 56 which interlocks with ridge 58 on the inner portion of the outer rim 60 of the housing 12. The outer tubular needle 18 is sealed by an 0-ring 62.

The inner tubular member 32 and suction outlet tube 16 are reciprocated by injecting a pulsating pressurized fluid, such as air, through the fluid inlet tube 23 and the fluid inlet port 22 into the fluid chamber 47. The pulses of increased pressure in the fluid chamber 47 cause the diaphragm 46 to push against the retainer 42 which is connected to the suction outlet tube 16. The retainer 42 and suction tube 16 are urged away from the fluid chamber 47 toward the stop ring 44, causing the spring 38 to be compressed and the inner tubular member 32 and blade 36 to slide toward the cutting position. When the pressure in the fluid chamber is reduced or released, the spring means 38 forces the retainer 42, the suction tube 16 and hence the blade 36 to the open position. The pressurized air source supplies air under pressure alternately between atmospheric pressure and an upper limit between 30 p.s.i. and 45 p.s.i. at any frequency selected by the user. A typical adjustable control mechanism allows the cutting blade 36 to cycle at any selected rate from 0-750 cutting strokes per minute (0-12.5 strokes per second).

The shape of the cutting blade 36, the outer end of the reciprocating inner tubular member 32, and the vitreous inlet port 20 are shown in FIGS. 4-7. As the blade 36 is reciprocated across the port 20, the cutting edge 37 of the blade 36 will slide across the outer or cutting edge 64 of the outer needle 18. The cutting edge 37 should be square; i.e. the cutting end of the inner tubular member 32 should be substantially perpendicular to its longitudinal axis.

Also, the cutting edge 64 of the aperture 20 is beveled or curved slightly toward the inner diameter cutting edge 65 to supply a clean entrance for the insertion of vitreous into the aperture 20 and an improved cutting action. Moreover, the inner edge 66 of the port is preferably concave away from the cutting edge 64 so that the blade 36 will be supported by the sides of the edge 66 as it is guided toward and over the cutting edge 64. The opposing edge 66 is also beveled to allow the entrance of the vitreous fibers into the port 20 to be viewed more easily by the surgeon.

The curvature of the cutting edge 64 may be formed simultaneously with the formation of the port 20. As illustrated in FIG. 3, a spherical drilling or grinding tool may be used to form the port 20 leaving a curved portion 64. The radius R in FIG. 3 illustrates this relationship. FIG. 5 illustrates the end of the inner hollow tubular member 32 and the blade 36. A slot or notch 68 is cut into the blade 36 on the side opposite the cutting edge 37. The blade is then flared at the end into an elliptical shape as is illustrated in FIGS. 5-7. The slot or notch 68 can be cut with a small rotating saw or the like, which will leave a small runout 69. The blade 36 is flared into an elliptical shape with a mandrel which is inserted in the open end of the cutting blade tubular member. The tube is formed or pressed in place around the mandrel. Thus, the cutting edge 37 of the blade 36 is slightly less rounded across the aperture 20 and will provide a more even cut along the length of the cutting edge 65 when the blade 36 is inserted into the outer hollow tube 18. By forming the end of the cutting blade 36 into an elliptical shape, the blade 36 will attempt to regain and retain that shape after it is inserted into the outer tube 18. Since there is only a few thousandths difference in the diameter of the mating tubular members, the force created by the inner tubular member attempting to form an elliptical shape inside a round tube will cause the cutting edge 37 of the blade 36 to precisely take the round cross-section of the corresponding part of the outer tube, i.e. across the inlet port 20, causing a tight shearing action. Further details of an exemplary needle 18, blade 36 and opening 20 may be found in U.S. Pat. No. 4,696,298 which is incorporated by reference herein.

In another embodiment of the present invention, tight shearing action is achieved by using a slightly bent blade as shown in FIGS. 8-10. As shown in FIG. 8, a blade insert 70 is inserted into the inner tubular member 32. The blade insert 70 may then be soldered to the inner tubular member 32. Blade insert 70 includes an end portion 72 that is angled outward toward aperture 20 when inserted into the needle 18. As shown in FIG. 9, this may be a five degree angle with respect to the central axis of the inner tubular member 32. As shown in FIG. 10, blade insert 70 is split at approximately its center line to form the half circle shape shown in FIG. 10. When blade insert 70 is inserted into needle 18, angle portion 72 will press against the inner wall of needle 18, thereby creating sufficient spring tension to hold the blade insert 70 into substantial conformity with the inner diameter of the outer needle 18 to create a tight shearing action across aperture 20.

In accordance with the present invention, as shown in FIG. 3, the needle 18 includes a transverse projection forming an extractor or dissector head 74 adjacent to the needle end 19. The dissector head 74 includes a flat bottom portion 76, extending continuously with the needle end 19. A ramp portion 78 extends from the end of the bottom 76 toward the opening 20. As shown in FIG. 12, when viewed from the bottom of the needle end 19, the dissector head 74 tapers at about a 60 degree angle toward the tip.

The dissector head 74 may be formed at the same time the end of the needle 18 is closed. For example, a "ball" of metal may be arc welded to the end of the needle 18. The "ball" may then be machined to form the desired shape. As shown in FIG. 3, arc welding leaves a slight radius of material on the inside of the end 19, but this does not effect the operation of the probe as the radius fits inside the open end of the blade 36.

Alternatively, as shown in FIG. 13, a premanufactured needle end 80 may be press fit inside the needle 18. This needle end 80 would include the aperture 20, the dissector head 74, needle end 19, and ramp 78. It should be noted that it is desirable to have the opening 20 as near as possible to the end 19 to facilitate the extraction of vitreous near objects such as the retina. Since the end of the needle 18 must be closed, however, it will be appreciated that the opening 20 must be some distance away from the end 19. Accordingly, the dissector head 74 facilitates extraction of vitreous close to the retina by lifting vitreous fibers and directing them up ramp 78 toward opening 20. Dissector head 74 may be used to literally scrape the surface of the retina, thereby forcing vitreous up ramp 78 into the opening 20. This will permit removal of vitreous immediately adjacent to the retina.

The needle 18 preferably is 25 gauge stainless steel. The outer tube diameter near the tip (needle end 19) is 0.5 mm. The tube is thin walled to allow maximum aspiration. The 0.45 mm port opening is 0.3 mm from the tip. The tube widens to a 20 gauge size (0.9 mm) approximately 10 mm from the tip to facilitate aspiration and prevent plugging.

In operation, vitreous which enters the aperture 20 is cut by the blade 36 and then enters the inner tubular member 32 due to the suction provided by the vacuum means (not shown). Vitreous matter then passes into the outlet tube 16, through the vacuum fitting 17, and into the vacuum tube 21. Vacuum fitting 17 is molded into the cap 26 and has an inside opening somewhat larger than the outlet tube 16 to permit reciprocating motion of the outlet tube 16 without making contact with the vacuum fitting 17. In this way, the reciprocating motion of outlet tube 16 is not transferred to the vacuum fitting 17, or to the vacuum tube 21. This improves the steadiness with which the probe 10 may be held by the ophthalmic surgeon. In some prior vitrectomy probes, the vacuum tube 21 was connected directly to the outlet tube 16 and the reciprocating motion of the outlet tube 16 was transferred to the vacuum tube 21 where the vibratory motion could be transferred to the hand of the surgeon. It is an advantage of the present invention to have all reciprocating motion completely internal to the probe 10.

While it will be apparent that the preferred embodiments of the invention disclosed are well calculated to fulfill the objects, benefits or advantages of the invention, it will be appreciated that the invention is susceptible to modification, variation and change without departing from the proper scope or fair meaning of the subjoined claims.

What is claimed is:

1. A microsurgical cutting device for cutting and removing fibrous gel, said device having a housing, a substantially hollow outer needle having an outward end with an aperture therein, a hollow tubular member having a cutting blade disposed within said outer needle an actuation means, and a suction means, said device comprising:

said housing containing a spring compartment and containing means for communicating with said actuation means, said spring compartment containing a compression spring acting against said actuation means;

said outer needle extending outwardly from said housing and containing said hollow tubular member reciprocable within said outer needle, said hollow tubular member communicating with said suction means a said cutting blade extending toward said apertured end of said outer needle;

said inner tubular member being reciprocable within said outer needle between a first open position and a second cutting position wherein said cutting blade slides across said apertured end of said outer needle, said actuation means tending to force said inner tubular member and cutting blade toward said second position and said compression spring tending to restore said inner tubular member and cutting blade to said first position;

adjustment means for adjusting the location of said inner tubular member when in said first open position;

tubular outlet port attached to said inner tubular member and communicating with said suction means;

tubular vacuum fitting extending outwardly from said housing and communicating with said vacuum means, said tubular vacuum fitting being isolated from the reciprocal motion of said tubular output port and said inner tubular member;

vacuum hose coupled to said suction means and attached to said tubular vacuum fitting; and said outer needle having at said outward end, a protrusion for facilitating the entry of said fibrous gel into said aperture.

2. The invention according to claim 1 wherein said adjustment means limits the motion of said inner tubular member toward said first open position by making contact with said actuation means at a predetermined location.

3. The invention according to claim 2 wherein said actuation means is a flexible diaphragm and said adjustment means is threadably adjustable within said housing.

4. The invention according to claim 1 wherein said tubular outlet port extends outwardly from said housing and is disposed partially within said tubular vacuum fitting.

5. The invention according to claim 1 wherein said tubular vacuum fitting is molded into said housing.

6. The invention according to claim 1 wherein said protrusion extends transversely from the outward end of said outer needle and tapers to a point, said protrusion including a ramp portion extending from said aperture toward said point.

7. The invention according to claim 1 wherein said outward end of said needle protrusion is press fit onto said needle.

8. The invention according to claim 1 wherein said cutting blade is elliptical in cross-section and said outer needle is circular in cross-section.

9. The invention according to claim 1 wherein said cutting blade includes an end portion that is bent toward said aperture.

10. The invention according to claim 9 wherein said end portion is semicircular in cross-section.

11. A microsurgical cutting device for cutting and removing fibrous gel, said device including a fingergrip, a substantially hollow outer needle having an open end disposed within said fingergrip and a substantially closed outer end extending from said fingergrip, said needle including an aperture near said closed end, a reciprocable tubular tool having a cutting end disposed within said needle, means for reciprocating said tool operatively connected to said tool, a suction means connected to the end of said tool opposite said cutting end, said device comprising:

adjustment means for reducing the size of said aperture by limiting the range of motion of said reciprocable tubular tool;

outlet port attached to said reciprocable tool and communicating with said suction means;

vacuum fitting extending outwardly from said fingergrip and isolated from the reciprocal motion of said outlet port and said tubular tool, and connected to said suction means; and said needle having a protrusion adjacent to said aperture for separating said fibrous gel from the retina prior to its cutting and removal by said device.

12. The invention according to claim 11 wherein said adjustment means is threadedly attached to said fingergrip and the range of reciprocable motion of said reciprocable tubular tool is adjusted by rotating said adjustment means.

13. The invention according to claim 11 wherein said outlet port extends outwardly from said fingergrip and is disposed partly within said vacuum fitting.

14. The invention according to claim 11 wherein said vacuum fitting is molded into said fingergrip.

15. The invention according to claim 11 wherein protrusion extends transversely from the outer end of said needle and tapers to a point, said dissector means including a ramp portion extending from said inlet aperture to said point.

16. The invention according to claim 15 wherein said taper is approximately a 60 degree taper, and said ramp is at approximately a 45 degree angle with respect to said closed end.

17. The invention according to claim 11 wherein said reciprocal tubular tool is elliptical in cross-section and said outer needle is circular in cross-section.

18. The invention according to claim 11 wherein said cutting end of said reciprocal tubular tool includes an end portion that is bent toward said aperture.

19. The invention according to claim 18 wherein said cutting end is semicircular in cross-section.

20. A microsurgical cutting device for cutting and removing fibrous gel, said device including a fingergrip, a substantially hollow outer needle having an open end disposed within said fingergrip and a substantially closed end extending from said fingergrip, said needle including an aperture near said closed end, a reciprocable tubular tool having a cutting end disposed within said needle, means for reciprocating said tool operatively connected to said tool, a suction means connected to the end of said tool opposite said cutting end, said device comprising:

outlet port attached to said reciprocable tool and communicating with said suction means;

vacuum fitting extending outwardly from said fingergrip and isolated from the reciprocal motion of said outlet port and said tubular tool, and connected to said suction means; and said needle having a protrusion adjacent to said aperture for separating said fibrous gel from the retina prior to its cutting and removal by said device.

21. A microsurgical cutting device for cutting and removing fibrous gel, said device including a fingergrip, a substantially hollow outer needle having an open end disposed within said fingergrip and a substantially closed end extending from said fingergrip, and needle including an aperture near said closed end, a reciprocable tubular tool having a cutting end disposed within said needle, means for reciprocating said tool operatively connected to said tool, a suction means connected to the end of said tool opposite said cutting end, said device comprising:

adjustment means for reducing the size of said aperture by limiting the range of motion of said reciprocable tubular tool;

outlet port attached to said reciprocable tool and communicating with said suction means; and said needle having a protrusion adjacent to said aperture for separating said fibrous gel from the retina prior to its cutting and removal by said device.

22. A microsurgical cutting device for cutting and removing fibrous gel, said device including a fingergrip, a substantially hollow outer needle having an open end disposed within said fingergrip and a substantially closed end extending from said fingergrip, said needle including an aperture near said closed end, a reciprocable tubular tool having a cutting end disposed within said needle, means for reciprocating said tool operatively connected to said tool, a suction means connected to the end of said tool opposite said cutting end, said device comprising:

outlet port attached to said reciprocable tool and communicating with said suction means; and said needle having a protrusion adjacent to said aperture for separating said fibrous gel from the retina prior to its cutting and removal by said device.

23. The invention according to claim 22 wherein said protrusion extends transversely from the axis of said needle.

24. The invention according to claim 23 wherein said protrusion comprises a ramp portion inclined toward said aperture.

25. The invention according to claim 24 wherein said protrusion tapers to point.

26. The invention according to claim 23 wherein said protrusion has a flat bottom.

* * * * *

UNITED STATES PATENT AND TRADEMARK OFFICE
CERTIFICATE OF CORRECTION

PATENT NO. : 5,047,008

DATED : September 10, 1991

INVENTOR(S) : Eugene de Juan, Jr., et al

It is certified that error appears in the above-identified patent and that said Letters Patent is hereby corrected as shown below:

Abstract, line 15; "faciitates" should be --facilitates--.

Column 1, line 20; "4,696,298" should be --4,698,298--.

Column 5, line 44; "4,696,298" should be --4,698,298--.

Column 7, line 15; after "means" delete "a" and insert --and having--.

Signed and Sealed this

Eleventh Day of May, 1993

Attest:

MICHAEL K. KIRK

Attesting Officer     Acting Commissioner of Patents and Trademarks